(12) United States Patent
Azimpour

(10) Patent No.: US 11,513,014 B2
(45) Date of Patent: Nov. 29, 2022

(54) ELECTRICAL ACTIVITY SENSOR WITH IMPROVED TEMPORAL AND SPATIAL ELECTRODE CONFIGURATION

(71) Applicant: Myia Labs, Inc., San Francisco (CA)

(72) Inventor: Farzad Azimpour, San Francisco, CA (US)

(73) Assignee: Myia Labs, Inc., San Francisco, CA (US)

( * ) Notice: Subject to any disclaimer, the term of this patent is extended or adjusted under 35 U.S.C. 154(b) by 139 days.

(21) Appl. No.: 16/844,295

(22) Filed: Apr. 9, 2020

(65) Prior Publication Data

US 2020/0326254 A1 Oct. 15, 2020
US 2022/0341800 A9 Oct. 27, 2022

Related U.S. Application Data

(60) Provisional application No. 62/832,112, filed on Apr. 10, 2019.

(51) Int. Cl.
*G01L 9/00* (2006.01)
*G06F 3/044* (2006.01)

(52) U.S. Cl.
CPC .......... *G01L 9/0072* (2013.01); *G06F 3/044* (2013.01)

(58) Field of Classification Search
None
See application file for complete search history.

(56) References Cited

U.S. PATENT DOCUMENTS

| | | | |
|---|---|---|---|
| 2012/0092279 A1* | 4/2012 | Martin | G06F 3/03547 345/173 |
| 2012/0092350 A1* | 4/2012 | Ganapathi | G06F 3/0446 345/501 |
| 2016/0220175 A1* | 8/2016 | Tam | A61B 5/486 |

* cited by examiner

*Primary Examiner* — Brandi N Hopkins
*Assistant Examiner* — Nigel H Plumb
(74) *Attorney, Agent, or Firm* — Nixon Peabody LLP

(57) ABSTRACT

The present disclosure provides an apparatus and a processing unit configured for sensing electrical activity with improved temporal and spatial electrode configuration. The apparatus includes a first layer configured to collect pressure data and a second layer comprising a plurality of electrodes configured to sense electrical activity. The processing unit is communicatively coupled to the apparatus to select a subset of the plurality of electrodes of the second layer from which electrical activity is measured based on an orientation of a user determined by received pressure data from the first layer. In an example, a body map of an individual can be produced from pressure distribution information received from the apparatus. This body map can then be used to select specific electrodes to measure the individual's electrical activity based on the body map pressure distribution information.

20 Claims, 11 Drawing Sheets

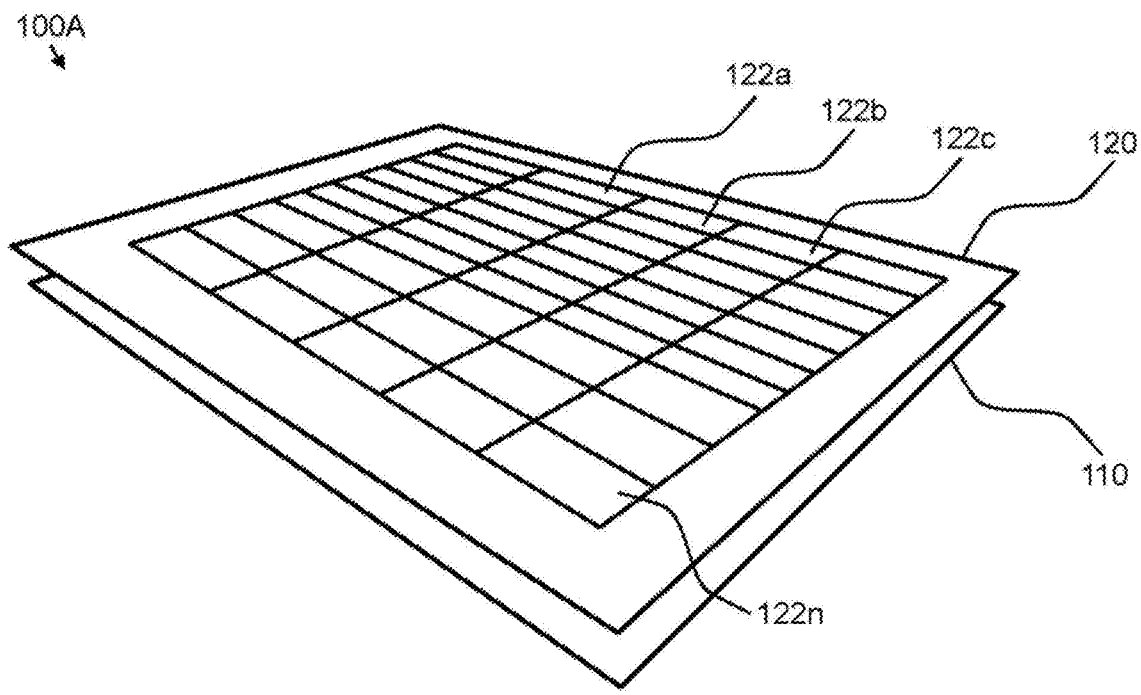
FIG. 1A
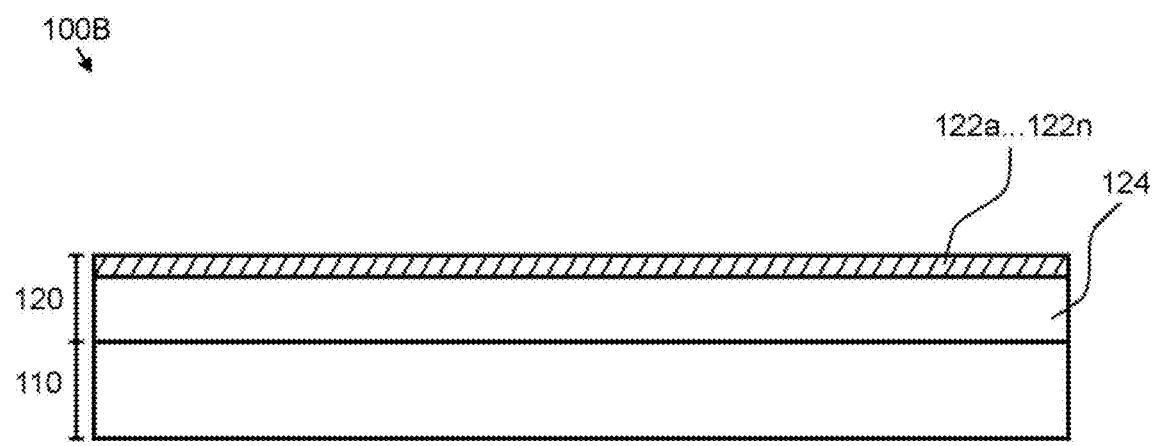
FIG. 1B
FIGS. 1A-1B

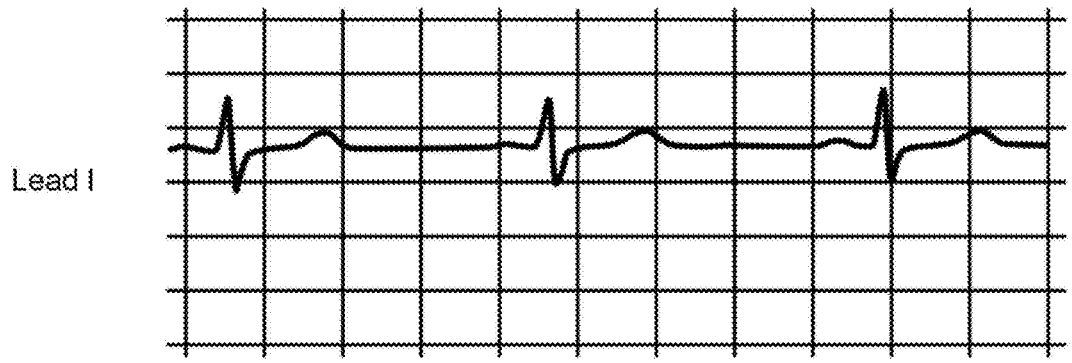
FIG. 5A
FIG. 5B
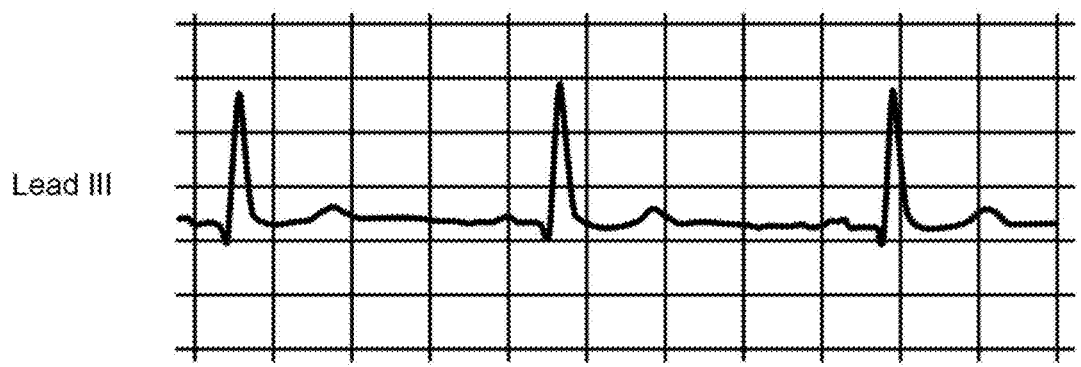
FIG. 5C
FIGS. 5A-5C

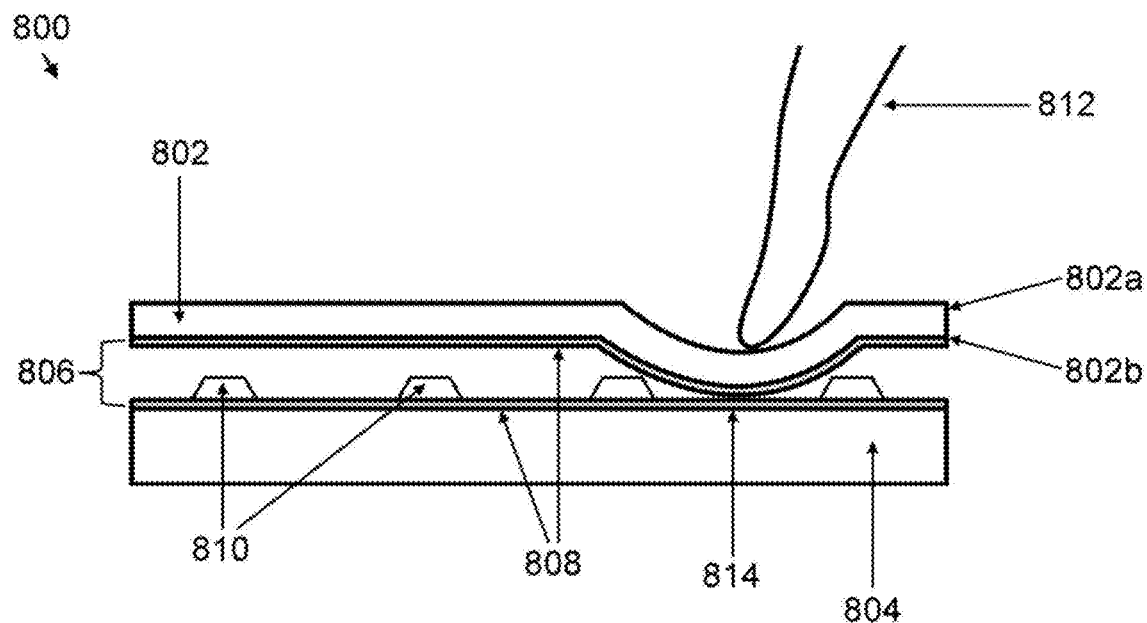
FIG. 8
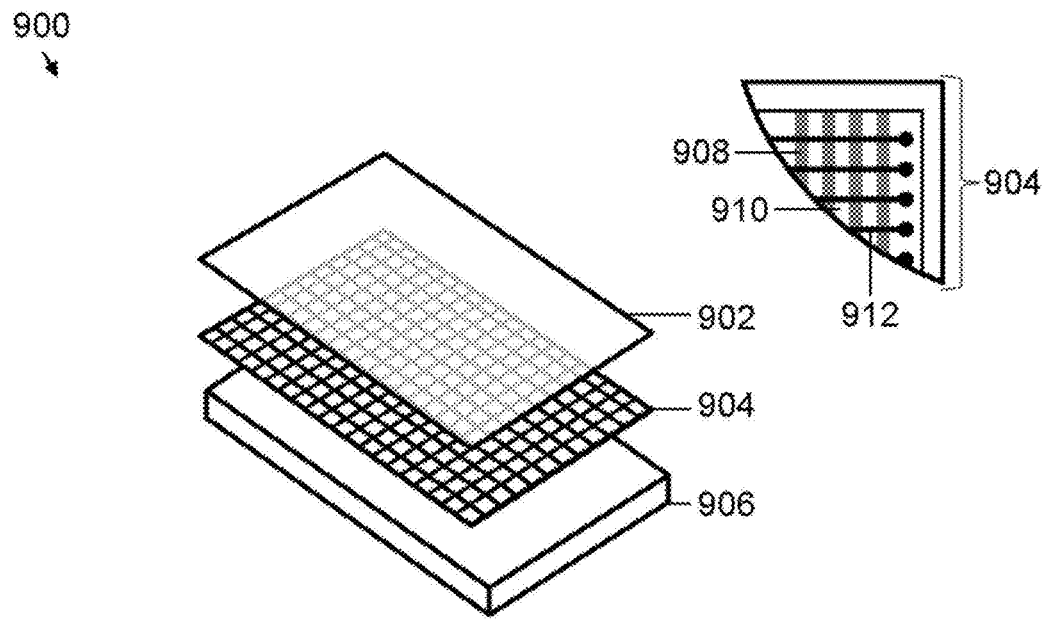
FIG. 9
FIGS. 8-9

ELECTRICAL ACTIVITY SENSOR WITH IMPROVED TEMPORAL AND SPATIAL ELECTRODE CONFIGURATION

CROSS REFERENCE TO RELATED APPLICATIONS

The present application claims the benefit of U.S. Provisional Patent Application 62/832,122 filed Apr. 10, 2019 and entitled "SYSTEMS AND METHODS FOR PASSIVELY MEASURING ELECTRICAL ACTIVITY," which is hereby incorporated by reference in its entirety.

FIELD

The present disclosure relates to systems and methods for passive measurement of electrical activity of a user.

BACKGROUND

A variety of health data can be provided from measuring electrical activity of a patient through electrodes placed on the patient's skin. In particular, an electrocardiogram (ECG) can be obtained using skin surface electrodes positioned on the patient's chest and some portion of the patient's extremities. Traditionally, a 12-lead ECG accounts for perpendicular vector arrays that are represented as "limb leads" and "precordial leads." More recently, the use of single-lead ECG (in the form of a chest-worn adhesive patch, independent or handheld unit, or smartwatch) has emerged as a clinically useful measure in patients undergoing evaluation for atrial (and some ventricular) arrhythmias, either to correlate symptoms with true arrhythmia presence, or to assess frequency and burden in those with defined arrhythmias (like atrial fibrillation and premature ventricular contractions (PVCs)).

SUMMARY

However, all conventional systems for measuring electrical activity based on skin surface electrodes either require (1) electrodes to be placed by a health professional in pre-determined locations on a patient's body, or (2) the patient to lie in a pre-determined position on a plurality of electrodes. Therefore, no systems or methods exist which can passively measure electrical activity of a patient without assistance from a health professional or communication to a patient regarding how the patient should position themselves. Therefore, what is needed are systems and methods to which can accurately measure electrical activity of a patient without oversight from a health professional.

A first embodiment of the present disclosure is directed a system comprising an apparatus and a processing unit. The apparatus includes a first layer and a second layer. The first layer is configured to collect pressure data, and the second layer comprises a plurality of electrodes configured to sense electrical activity. The processing unit is communicatively coupled to the apparatus and completes a series of steps. The steps provide for receiving pressure data from the first layer. Based on the received pressure data, the processing unit then determines an orientation of a user. The user can be positioned on the apparatus. The processing unit then selects a subset of electrodes from the plurality of electrodes, based on the determined orientation. The processing unit then measures electrical activity at the subset of electrodes.

In some examples of the first embodiment, the plurality of electrodes in the second layer are dry electrodes integrated into the second layer with woven conductive thread.

In some examples, the received pressure data is two-dimensional coordinates of pressure applied by the user to the first layer. In some examples, determining an orientation of the user can further include first placing the received pressure data in a coordinate grid. An exemplary coordinate grid corresponds to the first layer. The processing unit then identifies a body position of the user based on locations of the placed pressure data in the coordinate grid.

In some examples, identifying a body position of the user includes classifying the placed pressure data in the coordinate grid to generate a set of validated body positions for the user. The processing unit can classify the placed pressure data using a machine learning classifier to classify the placed pressure data as valid or invalid for each body position in a plurality of body positions. The processing unit can then output a set of valid body positions.

In some examples, when selecting a subset of electrodes, the processing unit selects corresponding electrodes based on the identified body position and the locations of the placed pressure data.

In some examples, measuring electrical activity includes generating a bipolar limb lead, a unipolar limb lead, and/or a unipolar chest lead.

In some examples, the apparatus is a bed sheet.

In some examples, based on the measured electrical activity, the processing unit can output an electrocardiogram, measured electrodermal activity, an electroencephalogram, and/or an electromyogram.

In some examples, the first layer includes a microelectromechanical system sensor, a board mounted sensor, and/or a heavy-duty pressure transducer.

A second embodiment of the present disclosure provides for a sheet and a processing unit. The sheet is configured to collect pressure data and comprises a plurality of electrodes. The sheet can a single layer. The processing unit is communicatively coupled to the apparatus and completes a series of steps. The steps provide for receiving pressure data from the sheet. Based on the received pressure data, the processing unit then determines an orientation of a user. The user can be positioned on the sheet. The processing unit then selects a subset of electrodes from the plurality of electrodes, based on the determined orientation. The processing unit then measures electrical activity at the subset of electrodes. Additional examples of the second embodiment can be as provided for with respect to the first embodiment.

A third example of the present disclosure provides for a methodology. The methodology can provide for receiving pressure data from an apparatus. The apparatus comprises a plurality of electrodes. The methodology then provides for determining an orientation of a user based on the received pressure data. The methodology then provides for selecting a subset of electrodes from the plurality of electrodes based on the determined orientation. The methodology then provides for measuring electrical activity at the subset of electrodes. The apparatus can be as provided for with respect to the apparatuses in the first or second embodiments. Additional examples of the third embodiment can be as provided for with respect to the first embodiment.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

BRIEF DESCRIPTION OF THE DRAWINGS

The accompanying drawings exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 1A shows an exploded view of an exemplary apparatus, according to an embodiment of the present disclosure.

FIG. 1B shows a cutaway view of an exemplary apparatus, according to an embodiment of the present disclosure.

FIGS. 5A-5C show exemplary measured electrical activity, according to an embodiment of the present disclosure.

FIG. 8 shows an exemplary resistive screen 800, according to an embodiment of the present disclosure.

FIG. 9 shows an exemplary capacitive screen 900, according to an embodiment of the present disclosure.

DETAILED DESCRIPTION

Figure 2:
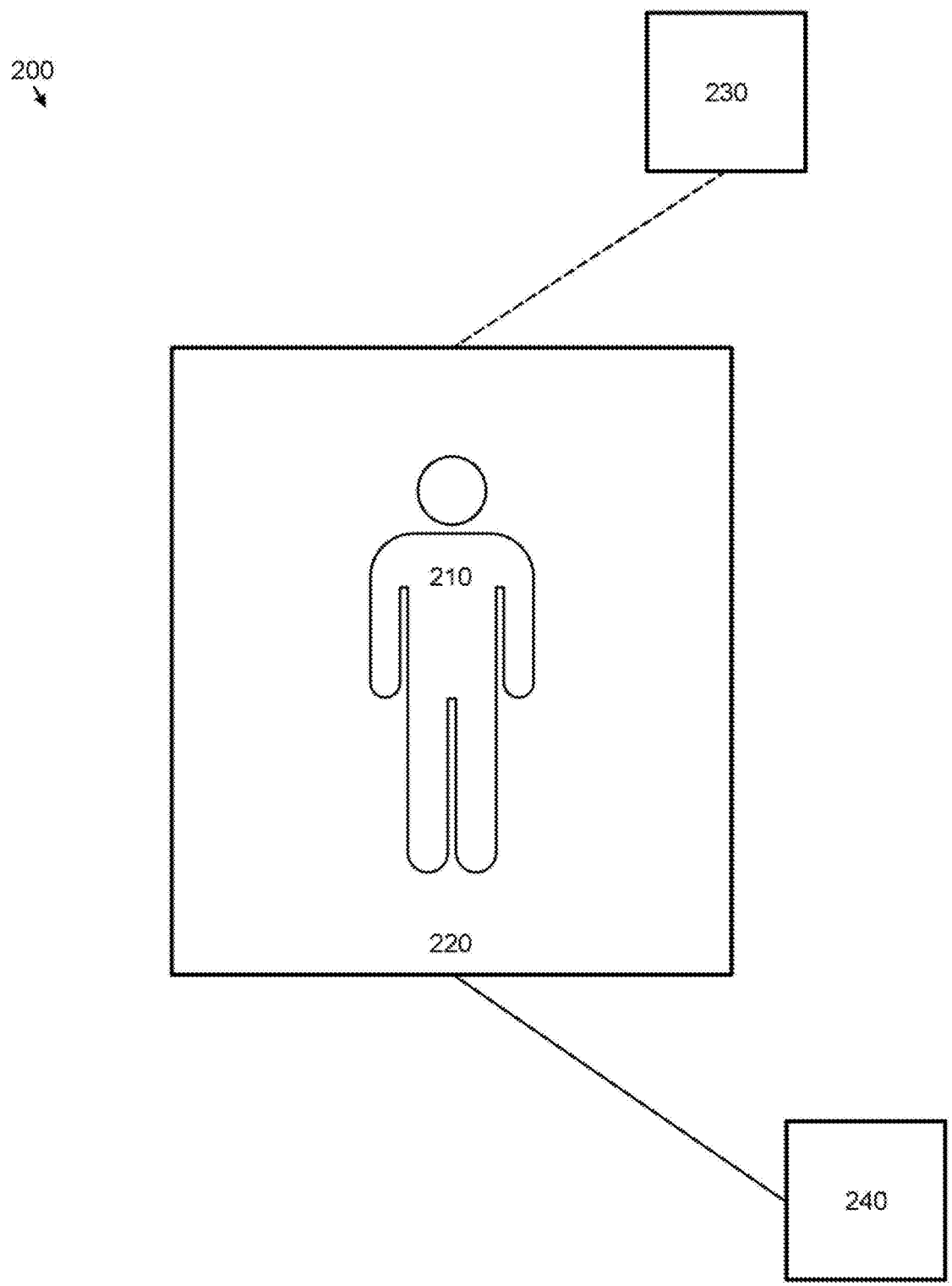
FIG. 2 shows an exemplary system, according to an embodiment of the present disclosure.

The present invention is described with reference to the attached figures, where like reference numerals are used throughout the figures to designate similar or equivalent elements. The figures are not drawn to scale, and are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details, or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The present disclosure is directed to systems and methods for sensing pressure distribution of a user and measuring electrical activity of the user based on the sensed pressure distribution. The present disclosure provides for an exemplary apparatus configured to sense pressure and measure electrical activity. An exemplary method can produce a body map of pressure distribution information received from the apparatus. The method can then select specific electrodes to measure a user's electrical activity based on the body map pressure distribution information.

Therefore, in some examples, the present disclosure provides an intelligent, passive, multi-lead-capable ECG lying surface, which captures electrocardiogram signals independent of specified body positioning or reliance on adhesive, wire-based electrodes.

FIG. 1A shows an exploded view 100A of an exemplary apparatus, according to an embodiment of the present disclosure. FIG. 1B shows a cutaway view 100B of the apparatus. FIGS. 1A-1B contain similar reference labels and elements and will be discussed in tandem. The apparatus of FIGS. 1A-1B can include a first layer 110 and a second layer 120 with a plurality of electrodes 122a, 122b, 122c, . . . 122n. In other examples, the apparatus can include a single layer.

The first layer 110 may collect pressure data, for example, from a user lying on the apparatus. In some examples, the first layer 110 includes sensors, such as a microelectromechanical system sensor, a board mounted sensor, a heavy-duty pressure transducer, or any other pressure sensor as known in the art. Therefore, the first layer 110 can sense the pressure distribution of a user while the user is lying, resting, or sleeping on the first layer 110.

In some other examples, the first layer 110 comprises several thin layers to form a resistive screen (shown in FIG. 8). In some other examples, the first layer 110 comprises a capacitive screen (shown in FIG. 9). In additional examples, the second layer 120 performs pressure sensing through the plurality of electrodes (discussed in further detail below).

The second layer 120 is configured to measure electrical activity, for example, from a user, through the plurality of electrodes 122a, 122b, 122c, . . . 122n. In some examples, the plurality of electrodes 122a, 122b, 122c, . . . 122n are an array of diffusely dispersed dry electrodes integrated with woven conductive thread (or other electrically conductive elements). In some examples, the electrodes 122a, 122b, 122c, . . . 122n can be controlled by an external computing device (not pictured). The electrodes 122a, 122b, 122c, . . . 122n can create a grid on the second layer 120 and can be operated synchronously or individually. In some examples, different combinations of the electrodes 122a, 122b, 122c, . . . 122n can be operated. For example, a particular subset of the electrodes 122a, 122b, 122c, . . . 122n can be chosen based on the external computing device (discussed further with respect to FIG. 3). Each electrode 122a, 122b, 122c, . . . 122n can be isolated in its sensing capabilities such that an electrode 122a, 122b, 122c, . . . 122n can be assigned an electric polarity while adjacent electrodes are transiently inactivated.

A user's skin should be in direct contact with the electrodes 122a, 122b, 122c, . . . 122n.

In some examples, the exemplary apparatus is a sheet, for example, a bedsheet. Although not pictured in FIGS. 1A-1B, the sheet can also be a single layer, where both the pressure sensors and the electrodes are integrated into one layer. In some examples, the single layer can include other sensing technology (discussed further below) configured to sense a body orientation of the user. The exemplary apparatus can be any other similar resting/sleep surface cover. For example, the exemplary apparatus can be made from plastic, fabric, bamboo, paper, and any other material as known in the art.

FIG. 2 shows an exemplary system 200, according to an embodiment of the present disclosure. System 200 can include a user 210, an apparatus 220, a computing device 230, and a power source 240.

The apparatus 220 can be as discussed above with respect to FIGS. 1A-1B. In particular, the apparatus 220 can be a sheet on which a user 210 can lie. The apparatus 220 can be attached to a power source 240. For example, the power source 240 can be a battery, an electrical outlet, or any other power source known in the art. The apparatus 220 can be communicatively coupled to a computing device 230. The apparatus 220 can be coupled to the computing device 240. For example, the apparatus 220 can send data from the pressure sensors or electrodes to the computing device 230. For example, the computing device 230 can activate particular electrodes on the apparatus 220. Additionally, the computing device 230 can control the apparatus as discussed further with respect to FIG. 3.

Figure 3:
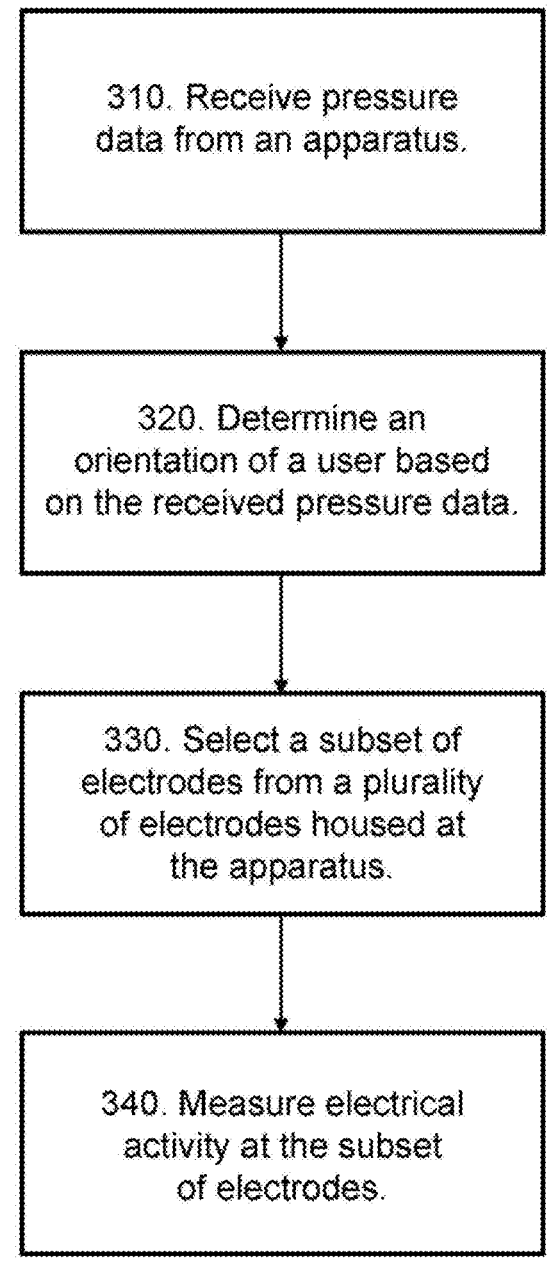
FIG. 3 shows an exemplary methodology for measuring electrical activity of a user, according to an embodiment of the present disclosure.

FIG. 3 shows an exemplary methodology 300 (e.g., a process) for measuring electrical activity of a user, according to an embodiment of the present disclosure.

Methodology 300 can begin at step 310 by receiving pressure data from an apparatus (for example, apparatus 220 of FIG. 2 or the apparatus shown in FIGS. 1A-1B). In some examples, the received pressure data can be received from the first layer and can be two-dimensional coordinates of pressure applied by the user to the first layer.

Methodology 300 can then proceed to step 320 and provide for determining an orientation of a user based on the received pressure data from step 310.

In some examples, determining an orientation of a user can include (1) placing the received pressure data in a coordinate grid (the coordinate grid corresponding to the first layer) and (2) identifying a body position of the user based on locations of the placed pressure data in the coordinate grid. Identifying a body position of the user can include classifying the placed pressure data in the coordinate grid to generate a set of validated body positions for the user. In some examples, classifying the placed pressure data can be performed by a machine learning classifier to classify the placed pressure data as valid or invalid for each body position in a plurality of body positions. For example, an external computing device can store a plurality of body positions, and the placed pressure data can be compared to the plurality of body positions. Additional examples of a machining learning classifier are discussed further below. The machine learning classifier can output a set of valid body positions.

In some examples, step 320 can be performed multiple times. The mapping information can be constantly updated throughout the course of the user's interaction with the surface, for example as the user changes positions or rolls from one side of the apparatus to the other. As a user's body position changes, different parts of their body make sufficient contact with the surface, and in some positions, not all extremities or body parts previously contacting the surface will continue to do so, for instance when a hand or arm rests over the abdomen as the person lies on their back. Therefore, this dynamic body pressure distribution coordinate data trains an intelligent computational model that is capable of identifying and discriminating between basic body part surfaces (like chest, back, left and right hands, arms, legs, and feet).

In some examples, step 320 can check the received pressure data against a database of calibration data. For example, a user can calibrate the apparatus to recognize positional variations in specific body part contact points. A computing device can additionally update the database with data generated at step 310. This exemplary database can represent the varieties of body positions allowing skin contact to the surface, represented as a dynamic set of coordinates of body pressure distribution. Additionally, the dataset can train an intelligent computational model that identifies various surface body parts and assigns them at least 2-dimensional coordinates.

The methodology 300 can then proceed to step 330 to select a subset of electrodes from the plurality of electrodes housed on the apparatus. The selected subset can be based on the determined orientation. In some examples, the selected subset includes corresponding electrodes based on the identified body position and the locations of the placed pressure data. For example, the electrodes can be selected in order to create proper leads. In an example, the electrodes can be selected to implement a particular electrocardiography lead or an approximation of such a lead, such as any of leads I, II, III, aVR, aVF, V1, V2, V3, V4, V5, and V6.

In some examples, electrodes can be selected corresponding to locations in the grid with a highest pressure reading. This can ensure that the selected electrodes have a high amount of direct contact with the skin of a user.

In some examples, step 330 can further provide for verifying that the selected subset of electrodes has an appropriate connection to the skin of a user. For example, step 330 can provide for verifying that the measured electrical activity comprises a resistance above a threshold resistance and/or detects an electrical charge. If any electrodes in the selected subset of electrodes do not have an appropriate connection to the skin of a user, step 330 can provide for replacing those electrodes (e.g., deselecting those electrodes and selecting alternate electrodes). In some examples, the electrodes can be replaced with adjacent electrodes.

The methodology 300 can then proceed to step 340 to measure electrical activity at the subset of electrodes. This can include generating a lead in the subset of electrodes, including a bipolar limb lead, a unipolar limb lead, a unipolar chest lead, or any other lead as known in the art. As used herein, generating a lead can include using selected electrodes to measure electrical activity along a vector through the target tissue (e.g., the heart).

For example, pressure mapping regions that correspond to the right and left arms can be assigned corresponding electrodes to generate a "lead I" ECG vector. Similarly, if the right arm and left leg are sensed as contacting the apparatus, they can be assigned to electrodes generate a "lead II" ECG vector.

In some embodiments of methodology 300, the method can further provide for outputting, based on the measured electrical activity, any of: (1) an electrocardiogram, (2) measured electrodermal activity of the user, (3) an electroencephalogram, and (4) an electromyogram.

Therefore, methodology 300 provides for temporal and spatial electrode orientation and assignment, which, in turn, allows for dynamic ECG lead (polarity) assignment and generation of multi-lead electrocardiogram tracings.

Figure 4A:
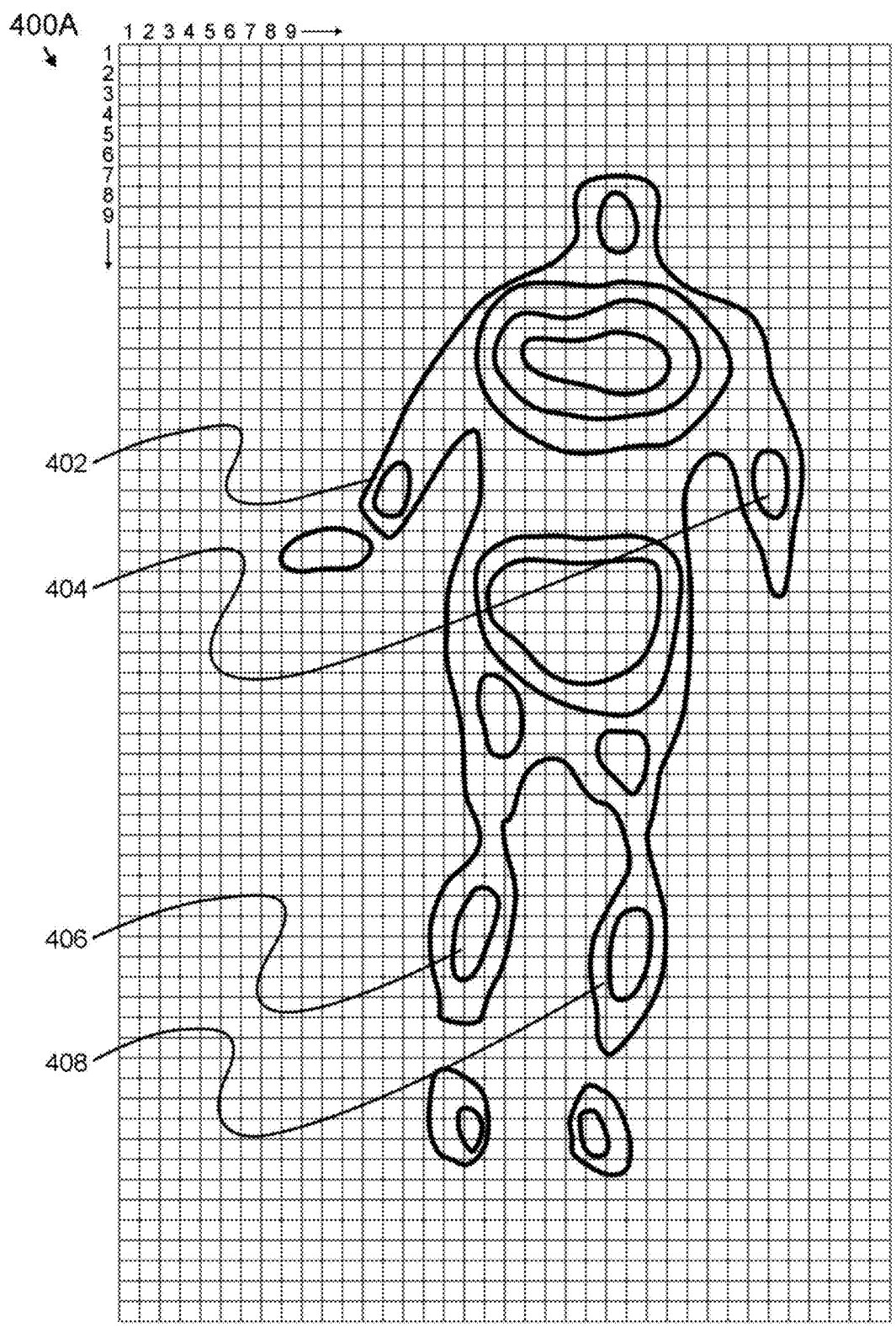
FIGS. 4A-4B show exemplary pressure sensor data, according to an embodiment of the present disclosure.
Figure 4B:
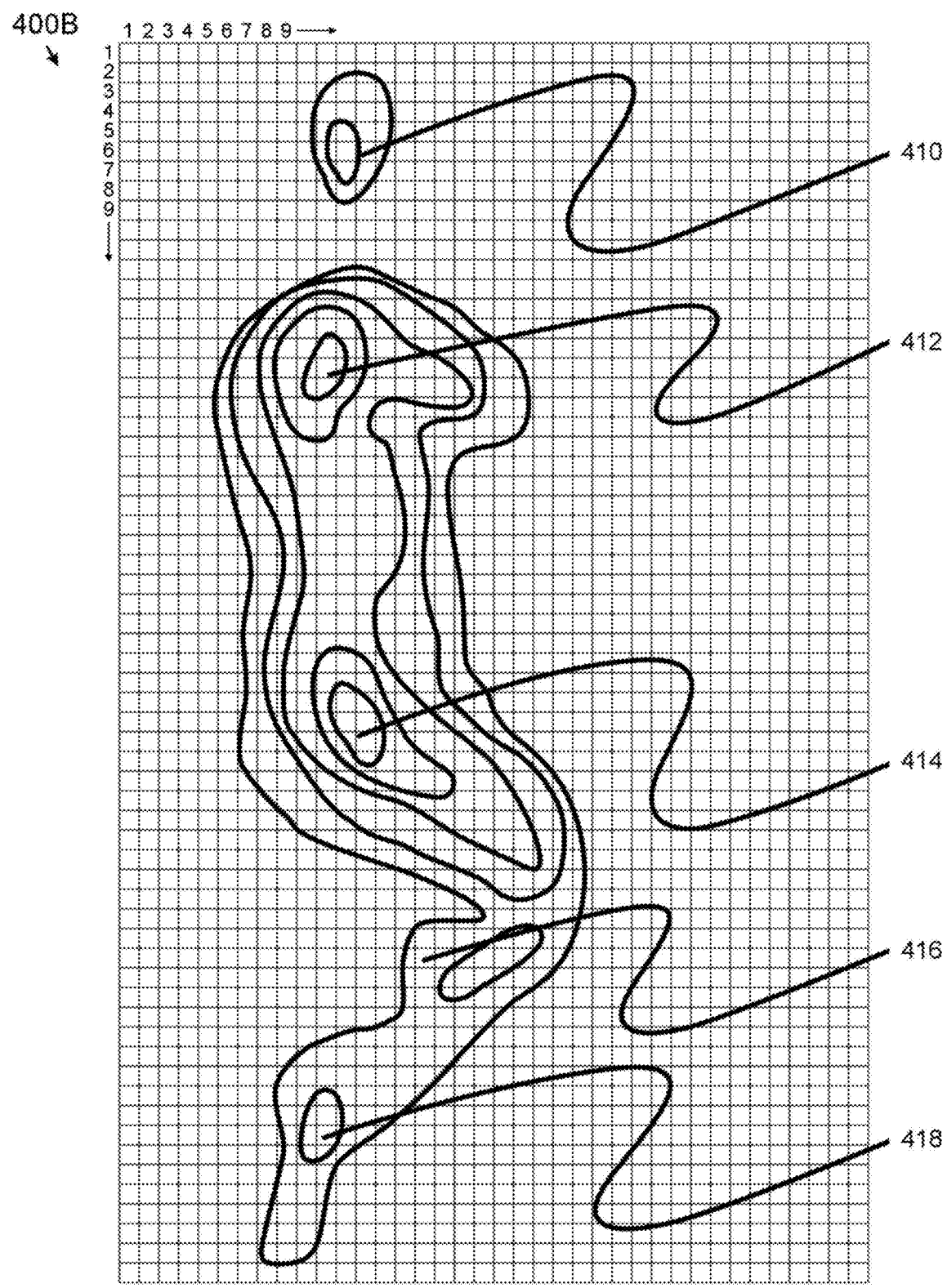

FIGS. 4A-4B show exemplary pressure sensor data, according to an embodiment of the present disclosure. The pressure sensor data depicted in FIGS. 4A and 4B can be mapped to the set of selectable electrodes (e.g., electrodes 122a, 122b, 122c, ... 122n in FIG. 1) of the apparatus. Thus, each selectable electrode can be associated with a certain region represented by the pressure sensor data. In an example, each individual box or set of several adjacent boxes depicted in the grids of FIGS. 4A and 4B can be associated with a unique selectable electrode, although other arrangements can be used. The resolution of the pressure sensor data does not need to necessarily match the resolution of available selectable electrodes.

FIG. 4A shows data 400A of an exemplary user lying on his back. An exemplary methodology, such as methodology 300 discussed above, can identify position 400A and can identify body parts of the user according to the sensor data. For example, the methodology can identify a right arm 402, a left arm 404, a right leg 406, and a left leg 406. The regions identified as right arm 402, left arm 404, right leg 406, and left leg 406 can be associated with respective selectable electrodes or respective subsets of selectable electrodes.

FIG. 4B shows data 400B of an exemplary user lying on his side. An exemplary methodology, such as methodology 300 discussed above, can identify position 400B and can identify body parts of the user according to the sensor data. For example, the methodology can identify a left face 410, a left shoulder 412, a left hip 414, a right heel 416, and a left foot 418. The regions identified as left face 410, left shoulder 412, left hip 414, right heel 416, and left foot 418 can be associated with respective selectable electrodes or respective subsets of selectable electrodes.

FIGS. 5A-5C show exemplary measured electrical activity, according to an embodiment of the present disclosure. For example, FIG. 5A shows electrical activity data when a bipolar lead I is generated between a right arm and a left arm, according to an embodiment of the present disclosure. This electrical activity data can be based on electrodes that were dynamically selected as being associated with a detected right arm (e.g., right arm 402 of FIG. 4A) and a detected left arm (e.g., left arm 404 of FIG. 4A). Therefore, FIG. 5A demonstrates the ability of the present disclosure to measure electrical activity of a user without a health professional positioning the user.

For example, FIG. 5B shows electrical activity data when a bipolar lead II is generated between a right arm and a left leg, according to an embodiment of the present disclosure. This electrical activity data can be based on electrodes that were dynamically selected as being associated with a detected right arm (e.g., right arm 402 of FIG. 4A) and a detected left leg (e.g., left leg 408 of FIG. 4A). Therefore, FIG. 5B demonstrates the ability of the present disclosure to measure electrical activity of a user without a health professional positioning the user.

For example, FIG. 5C shows electrical activity data when a bipolar lead I is generated between a left shoulder and a right foot, according to an embodiment of the present disclosure. This electrical activity data can be based on electrodes that were dynamically selected as being associated with a detected left shoulder and a detected right foot. Therefore, FIG. 5C demonstrates the ability of the present disclosure to measure electrical activity of a user without a health professional positioning the user.

Machine Learning

Various aspects of the present disclosure can be performed by a machine-learning algorithm, as readily understood by a person skilled in the art. In some examples, the step 320 of FIG. 3 can be performed by a supervised or unsupervised algorithm. For instance, the system may utilize more basic machine learning tools including 1) decision trees ("DT"), (2) Bayesian networks ("BN"), (3) artificial neural network ("ANN"), or (4) support vector machines ("SVM"). In other examples, deep learning algorithms or other more sophisticated machine learning algorithms, e.g., convolutional neural networks ("CNN"), or capsule networks ("CapsNet") may be used.

DT are classification graphs that match input data to questions asked at each consecutive step in a decision tree. The DT program moves down the "branches" of the tree based on the answers to the questions (e.g., First branch: Is there a large flat area in the pressure data? yes or no. Branch two: Does the pressure data also include a thin extension of data extending from the large flat area? yes or no, etc.).

Bayesian networks ("BN") are based on likelihood something is true based on given independent variables and are modeled based on probabilistic relationships. BN are based purely on probabilistic relationships that determine the likelihood of one variable based on another or others. For example, BN can model the relationships between location data, time stamp data, previous alerts, and any other information as contemplated by the present disclosure. Particularly, if a user's pressure data from the sheet is known, a BN can be used to compute what valid body positions the user can be in based on the pressured data. Thus, using an efficient BN algorithm, an inference can be made based on the input data.

Artificial neural networks ("ANN") are computational models inspired by an animal's central nervous system. They map inputs to outputs through a network of nodes. However, unlike BN, in ANN the nodes do not necessarily represent any actual variable. Accordingly, ANN may have a hidden layer of nodes that are not represented by a known variable to an observer. ANNs are capable of pattern recognition. Their computing methods make it easier to understand a complex and unclear process that might go on during predicting a body position of the user based a variety of input data.

Support vector machines ("SVM") came about from a framework utilizing of machine learning statistics and vector spaces (linear algebra concept that signifies the number of dimensions in linear space) equipped with some kind of limit-related structure. In some cases, they may determine a new coordinate system that easily separates inputs into two classifications. For example, a SVM could identify a line that separates two sets of points originating from different classifications of events.

Deep neural networks (DNN) have developed recently and are capable of modeling very complex relationships that have a lot of variation. Various architectures of DNN have been proposed to tackle the problems associated with algorithms such as ANN by many researchers during the last few decades. These types of DNN are CNN (Convolutional Neural Network), RBM (Restricted Boltzmann Machine), LSTM (Long Short Term Memory), etc. They are all based on the theory of ANN. They demonstrate a better performance by overcoming the back-propagation error diminishing problem associated with ANN.

Machine learning models require training data to identify the features of interest that they are designed to detect. For instance, various methods may be utilized to form the machine learning models, including applying randomly assigned initial weights for the network and applying gradient descent using back propagation for deep learning algorithms. In other examples, a neural network with one or two hidden layers can be used without training using this technique.

In some examples, the machine learning model can be trained using labeled data, or data that represents certain user input. In other examples, the data will only be labeled with the outcome and the various relevant data may be input to train the machine learning algorithm.

For instance, to determine whether a particular regulation fits the input data, various machine learning models may be utilized that input various data disclosed herein. In some examples, the input data will be labeled by having an expert in the field label the relevant regulations according to the particular situation. Accordingly, the input to the machine learning algorithm for training data identify various legal regulations as 'relevant' or 'non-relevant'.

Cardiac Sensor Device and System Configurations

FIGS. 6A through 6D of the drawings show non-limiting examples of cardiac sensor device and system configurations. As indicated above, each of the systems and devices depicted and discussed with respect to FIGS. 6A-6D can take on any of the other various forms, optional configurations, and functional alternatives described with respect to the other disclosed embodiments, unless explicitly disclaimed or otherwise logically prohibited. An example cardiac sensor device, designated generally at 600A in FIG. 6A, includes a data receiver 601 disposed on or in a substrate 600. For example, the substrate 600 can be the second layer 120 of FIGS. 1A-1B. The substrate 600 and/or the data receiver 601 can be configured to be in contact with a portion of body tissue, including tissue proximate to cardiac tissue, or any other tissue in communication with the heart, or other portion of the body related to cardiac activity, including any portion of a subject's skin, to which the data receiver 601 and the substrate 600 are in contact. The object is a body part, a secondary object, and/or a muscle group, for example. In another example, the object can be the user's skin on any body part (for example, the leg, the arm, the chest, the back, the face, the neck, the stomach, and any other body part.).

Data receiver 601 can include one or more of any conformal sensor components according to the principles of any of the examples and/or figures described herein. In an example, the data receiver 601 includes a ECG component 603 and at least one other measurement component 604. Measurement component 604 can include, in at least some implementations, an accelerometer, a heart rate monitor (including a muscle activation monitor), and/or any other sensor known in the art. The data receiver 601 can be the plurality of electrodes 122a, 122b, 122c, . . . 122n as discussed above with respect to FIGS. 1A-1B. The at least one ECG component 603 and/or at least one measurement component 604 can be used to measure data indicative of a cardiac activity (including at a portion of cardiac tissue or any other tissue in communication with the heart, or other portion of the body related to cardiac activity). In some examples, the ECG component can be connected to a user's body part, a secondary object, and/or a muscle group. The secondary object can be the user's skin on any body part (for example, the leg, the arm, the chest, the back, the face, the neck, the stomach, and any other body part).

Figure 6A:
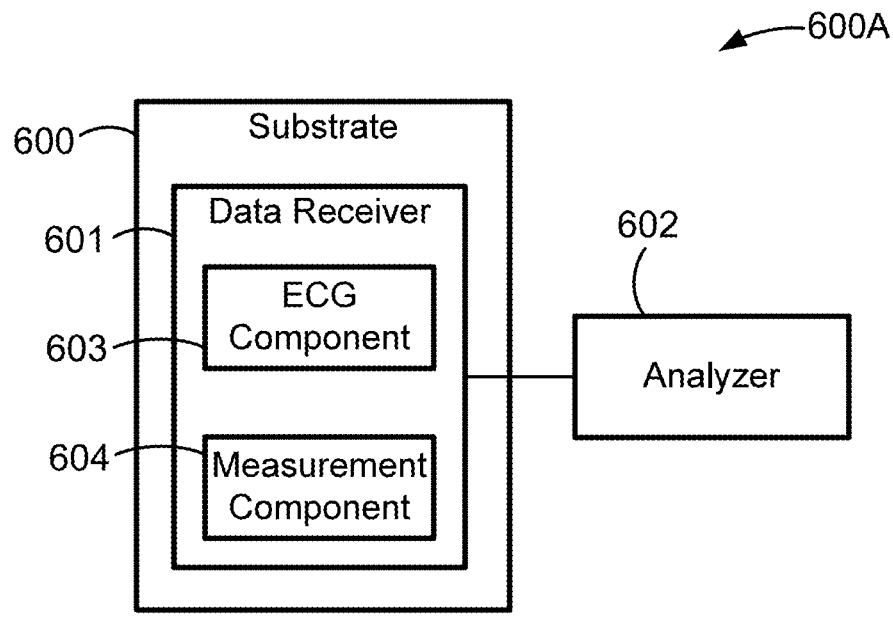
FIGS. 6A-6D show systems and devices for monitoring the cardiac activity of an individual in accordance with aspects of the present disclosure.

The example device of FIG. 6A also includes an analyzer 602. As illustrated, the analyzer 602 is configured to quantify the data indicative of cardiac activity, other physiological data, and/or analysis of such data indicative of cardiac activity, and/or physiological data, according to the principles described herein. In one example, the analyzer 602 is disposed on or in the substrate 600 with the data receiver 601, while in another example the analyzer 602 is disposed proximate to or remote from the substrate 600 and data receiver 601. In the representative implementation of the device in FIG. 6A, the analyzer 602 is configured to quantify or otherwise analyze the data indicative of the ECG measurement and/or the other component measurement (such as an accelerometer measurement, a heart rate measurement, and/or muscle activation monitoring) to provide an indication of cardiac activity. Analyzer 602 of FIGS. 6A-6D includes, as some non-limiting examples, a central processing unit (CPU), one or more microprocessors (e.g., a master processor, a slave processor, and a secondary or parallel processor), and/or any combination of hardware, software, or firmware disposed resident to or remote from the sensor device.

Figure 6B:
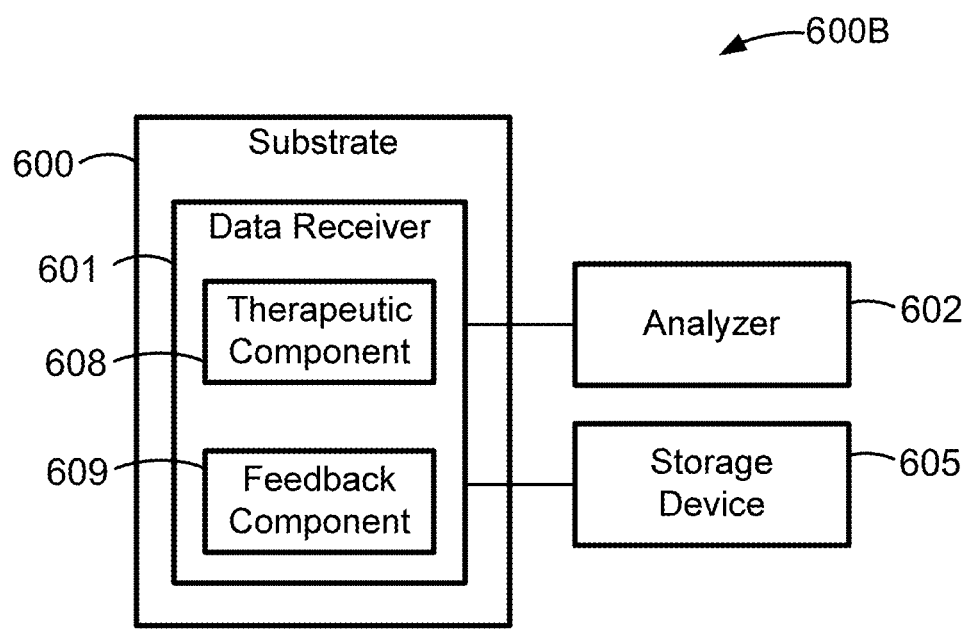

FIG. 6B shows another representative cardiac sensor device 600B, which includes a substrate 600, a data receiver 601, an analyzer 602, and a storage module 605. Optionally, the device 600B may further comprise a therapeutic component 608 and/or a feedback component 609. Therapeutic component 608 may utilize the data received by data receiver 601 and analyzed by the data analyzer 602 to provide therapeutic, pharmacological or other medicinal treatment to the user. Conversely, feedback component 609 may utilize the data received by data receiver 601 and analyzed by the data analyzer 602 to provide diagnostic information, physiological information and/or other feedback on cardiac activity and/or other electrophysiological measurements to the user regarding, e.g., any of the characteristics identified in FIGS. 3-5C. The storage module 605 illustrated in FIG. 6B is configured, for example, to include a memory to save data from the data receiver 601 and/or the analyzer 602. In some implementations, the storage device 605 is any type of non-volatile memory. Any of the storage devices 605 illustrated in the drawings can include flash memory, solid state drives, removable memory cards, erasable programmable read only memory (EEPROM), random access memory (RAM), or any other type of computer-readable medium, or any combination thereof. In certain examples, the storage device 605 is removable from the device. In some implementations, the storage device 605 is local to the device while in other examples it is remote. For example, the storage device 605 can be the internal memory of a computing device. In the various examples herein, the computing device may be a smartphone, a personal computer, a tablet computer, a slate computer, a personal digital assistant (PDA), an e-reader or other electronic reader, an Xbox®, a Wii®, or other game system(s), or other hand-held or worn computing device. In this example, the device may communicate with the external computing device via an application executing on the external computing device. In some implementations, the sensor data can be stored on the storage device 605 for processing at a later time. In some examples, the storage device 605 can include space to store processor-executable instructions that are executed any of the disclosed methods, functions, and operations, including to analyze data from the data receiver 601. In other examples, the memory of the storage device 605 can be used to store the measured data indicative of cardiac activity, other physiological data, or analysis of such data indicative of cardiac activity, or physiological data, according to the principles described herein.

Figure 6C:
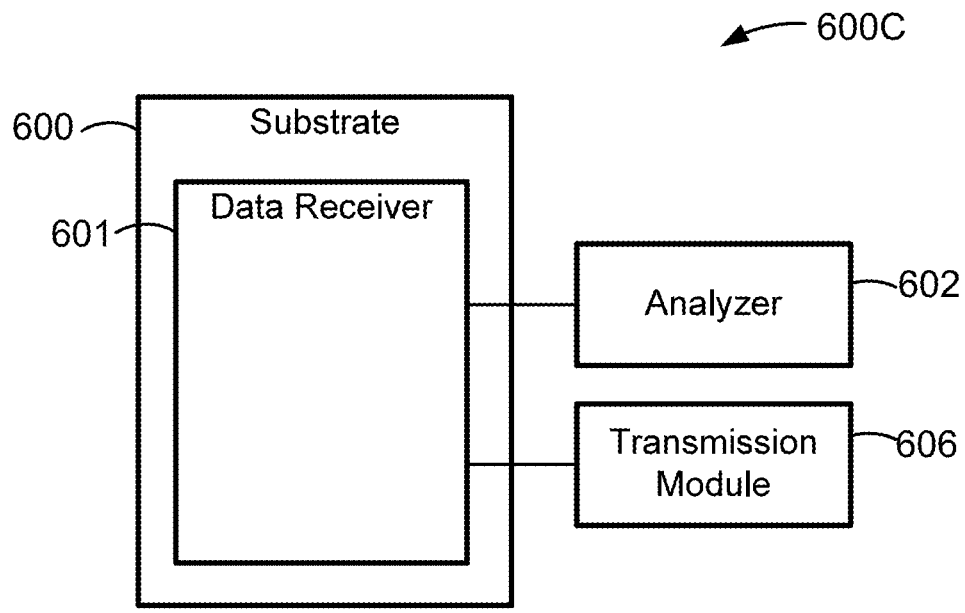

FIG. 6C shows yet another example of a cardiac sensor device 600C according to the principles disclosed herein. Sensor device 600C includes, for example, a substrate 600, a data receiver 601, an analyzer 602, and a transmission module 606. The transmission module 606 is configured to transmit data from the data receiver 601, the analyzer 602, and/or stored in a storage device (such as the storage device 605 of FIG. 6B), to an external memory or other storage device, a network, and/or an off-board computing device. In an example, the transmission module 606 can be a wireless transmission module. For such configurations, the transmission module 606 transmits data via wireless networks, radio frequency communication protocols, Bluetooth®, near-field communication (NFC), and/or optically using infrared or non-infrared LEDs. The data can be transmitted to an external memory or other storage device, a network, and/or an off-board computing device.

Figure 6D:
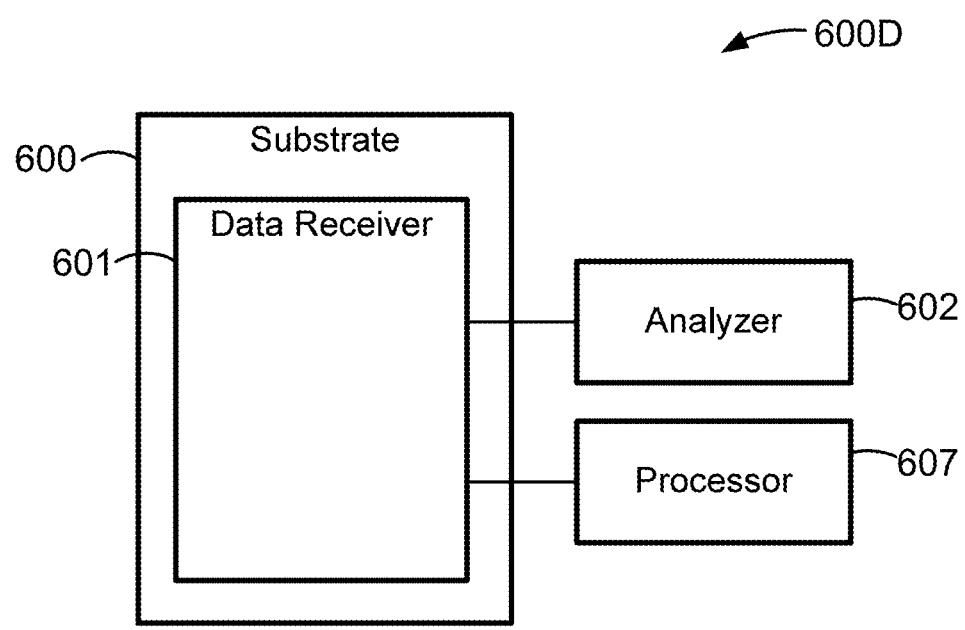

FIG. 6D shows yet another example system 600D that includes a substrate 600, a data receiver 601, an analyzer 602, and a processor 607. The data receiver 601 can receive data related to sensor measurement(s) from a sensor. In some examples, the sensor can be any of: a conformal sensor, an electrode, a dry electrode, a wearable electrode, or any other as known in the art. The processor 607 is configured, for example, to execute processor-executable instructions stored in a storage device 607 and/or within the processor 607 to analyze data indicative of cardiac activity, other physiological data, or analysis of such data indicative of cardiac activity, or other physiological data according to the principles described herein. In some implementations, the data can be directly received from the data receiver 601 or retrieved from a storage device (such as the storage device 605 of FIG. 6B). In one example, the processor is a component of the analyzer 602 and/or disposed proximate to the data receiver 601. In another example, the processor 607 is external to the system, such as in a computing device that downloads and analyzes data retrieved from the system. The processor 607 can execute processor-executable instructions that quantify the data received by the data receiver 601.

In some cases, a system can include any suitable combination of the elements of system 600A, system 600B, system 600C, and/or system 600D. For example, a system can include a transmission module (e.g., transmission module 606 of FIG. 6C) and a therapeutic component (e.g., therapeutic component 608 of FIG. 6B).

Figure 7A:
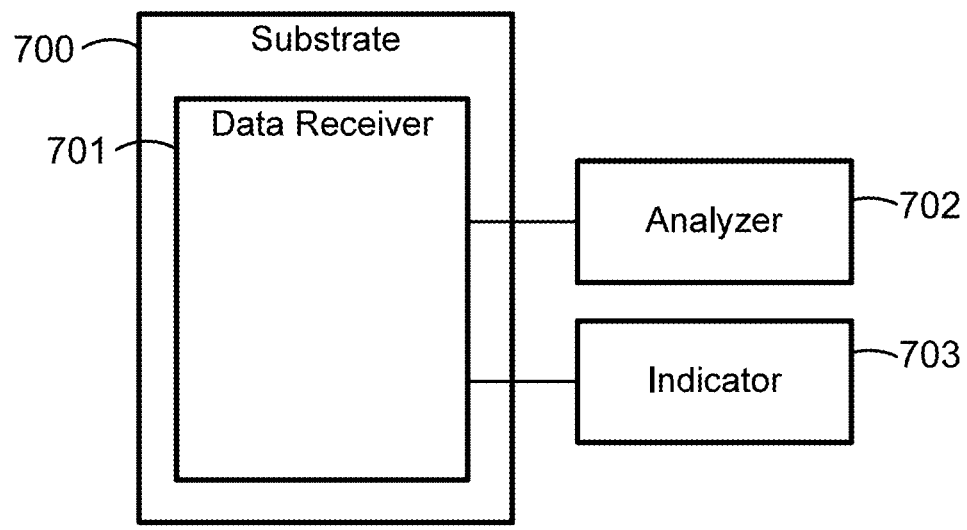
FIGS. 7A-7C show block diagrams illustrating examples of systems and devices for monitoring the cardiac activity of an individual and displaying data indicative of such cardiac activity in accord with aspects of the present disclosure.
Figure 7B:
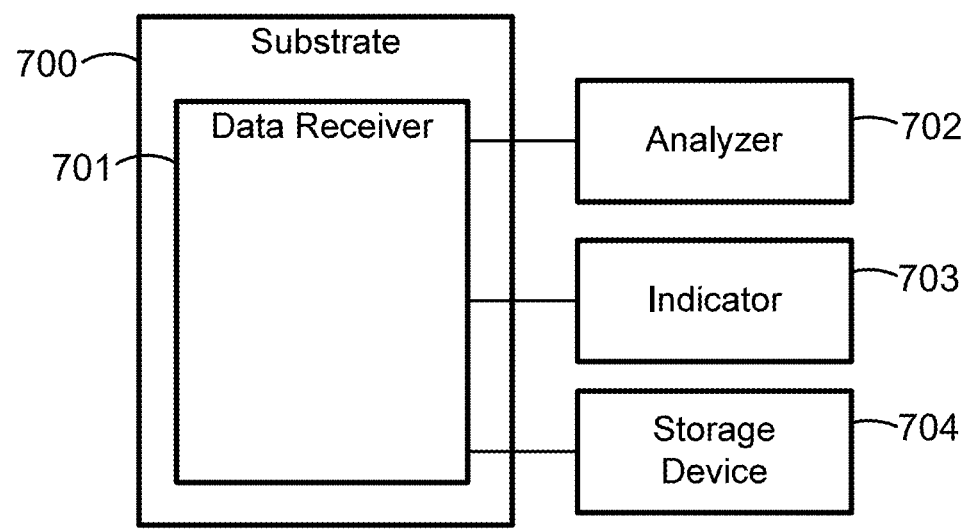
Figure 7C:
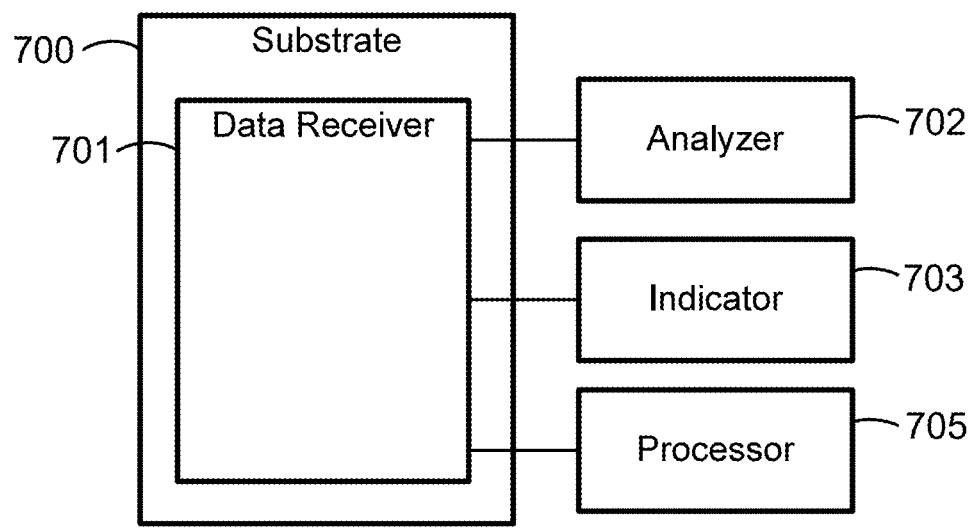

FIGS. 7A-7C show non-limiting examples of cardiac sensor system configurations that include an electronic display or other output device for displaying or otherwise outputting the data or analysis results from analysis of the data. The example systems of FIGS. 7A-7C include a substrate 700, a data receiver 701, an analyzer 702, and a display 703. As shown in the examples of FIGS. 7B-7C, the system can further include a processor 705 (see FIG. 7C), to execute the processor-executable instructions described herein, and/or a storage device 704 (see FIG. 7B), for storing processor-executable instructions and/or data from the analyzer 702 and/or one or more conformal sensors of the system.

The display 703 of the example systems of FIGS. 7A-7C can be used for displaying and/or transmitting data indicative of cardiac activity, other physiological data, and/or analysis of such data indicative of cardiac activity, or other physiological data, according to the principles described herein, and/or user information. In one example, the display 703 can comprise a liquid crystal display (LCD) device, a light emitting diode (LED) display device, or an electrophoretic display (such as e-ink), and/or a plurality of indicator lights. For example, the display 703 can include a series of LEDs. In some implementations, the LEDs range in color, such as from green to red. In this example, if performance does not meet a pre-determined threshold measure, a red indicator light can be activated and if the performance meets the pre-determined threshold measure, the green indicator light can be activated. In another example, display 703 may include a screen or other display that can be used to display graphs, plots, icons, or other graphic or visual representations indicative of the data or analysis results from analysis of the data.

In some implementations, as described above, the signaling of the display 703 is detectable to the human eye; in other implementations, it is not detectable by the human eye but can be detected using an image sensor. The display 703 may be configured to emit light outside the visible spectrum of the human eye (e.g., infrared) or to emit light that is too dim to be detected, as examples of indication methods substantially not detectable by the human eye. In these examples, the image sensor can be configured to detect such signals outside the viewing capabilities of a human eye. In various examples, the image sensor may be a component of a smartphone, a tablet computer, a slate computer, an e-reader or other electronic reader or hand-held or wearable computing device, a laptop, an Xbox®, a Wii®, or other game system(s).

In some cases, a system can include any suitable combination of the elements of system 700A, system 700B, and/or system 700C. For example, a system can include a storage device (e.g., storage device 704 of FIG. 7B) and a processor (e.g., processor 705 of FIG. 7C).

Body Orientation Sensing Technologies

FIG. 8 shows an exemplary resistive screen 800 which can be used in various embodiments of the present disclosure. For example, the exemplary resistive screen 800 can be the first layer 110 of FIG. 1A. The exemplary resistive screen 800 includes a first layer 802, a second layer 804, a gap 806, coating 808, conductive connections 810, and a finger 812. The first layer 802 and the second layer 804 can be two transparent electrically resistive layers, facing each other with a thin gap 806 in-between. The first layer 802 can have a first surface 802a that a user interacts with (as shown, for example, by the finger 812). For example, the user can lay on the first surface 802a. The first layer 802 further comprises a coating 808 on an underside surface 802b. The second layer 804 is a similar resistive layer, with a coating 808. The second layer 804 also includes conductive connections 810 along its sides. In some examples (not pictured), the first layer 802 also includes conductive connections 810. The conductive connections 810 can be spacer dots or insulating pads, for example.

Therefore, a resistive screen can identify a voltage as applied to one layer (e.g., first layer 802), and sensed by the other layer (e.g., second layer 804). When an object, such as a fingertip 812, presses down onto the outer surface, the first layer 802 and the second layer 804 touch to become connected at that location 814. For example, when a person lies down on a resistive screen 800, multiple locations 814 can be created with various voltages. The present disclosure contemplates that the body part of an individual interacting with the resistive screen 800 can be identified (for example, by computing device 230 of FIG. 2) according to the location 814 and the voltage generated by the interaction.

FIG. 9 shows an exemplary capacitive screen 900 which can be used in various embodiments of the present disclosure. For example, the capacitive screen 900 can be the first layer 110 of FIG. 1A. The capacitive screen 900 includes a protective cover 902, a substrate 904, a base material 906, sensing lines 908, insulating material 910, and driving lines 912. The capacitive screen 900 includes two primary layers: (1) a protective cover 902, which acts as a surface insulator, and (2) a substrate 904, which acts as a conductive layer beneath the protective cover 902. In some examples, the screen 900 can further include a base material 906. The base material 906 can provide structural support to the capacitive screen, and, in some examples, can be the second layer 120 of FIG. 1A. The sensing lines 908 and the driving lines 912 for perpendicular tracks to form a grid. The lines 908 and 812 can be separated by insulating material 910.

Because the human body itself is an electrical conductor, when the screen 900 is touched with any human body part, an electrostatic field of the screen 900 is distorted. The present disclosure contemplates that this distortion can be located on the screen 900 along the grid created by the perpendicular sensing lines 908 and driving lines 912 (for example, by the computing device 230 of FIG. 2). A capacitive screen 900 can also accept multi-touch interactions and require less physical force to register a touch, than their resistive screen counterparts (e.g., screen 800 of FIG. 8).

In other examples of the present disclosure, micro-patterned electrodes can be used as a form of capacitive screen 900 to provide both (1) the pressure-sensing technology of layer 110 of FIG. 1A, and (2) the electrical activity measurement technology of layer 120 of FIG. 1A. In such an example, an apparatus according to the present disclosure includes only one integrated mechanism (for example, screen 900 of FIG. 9) and does not include two distinct layers for separate functions (for example, as in FIG. 1A).

Determining Respiratory Rates

In another example of the present disclosure, the disclosed apparatus and system measure respiratory rates of a user. For example, when a user lies on the disclosed apparatus, the system identifies a position of the user on the apparatus. The system then identifies a location on the apparatus corresponding to the user's chest. For example, this location corresponds to a portion of the coordinate grid discussed with respect to FIG. 1. The system then tracks breathing movements of the user based on changes in data received at that location.

In one example of tracking breathing movements, the system evaluates (1) a level of force exerted by the user at the identified location on the apparatus and (2) a surface area of the pressure at the identified location on the apparatus. For example, a greater force and a greater surface area of the pressure corresponds to an inhale; a decrease in the force and a decrease in the surface area of the pressure corresponds to an exhale.

In another example of tracking breathing movements, the system tracks respiratory rates through the plurality of electrodes disposed on the apparatus. The system selects electrodes from locations on the grid of the apparatus corresponding to the user's chest. These selected electrodes record data from the surface of the user's chest; this data is influenced by (1) motion of the electrodes with respect to the heart, and (2) by changes in electrical impedance of the chest. The expansion and contraction of the chest during respiration results therefore causes movement of the selected electrodes. The electrical impedance of the chest is also changed by the filling and emptying of the lungs during respiration (the heart moves according to the respiration, changing the amplitude and vector of the electrode signals). These physical influences of respiration result in amplitude variations in data collected by the corresponding electrodes; this amplitude variation can be used to deduce respiratory rates. In particular, the R-waves of the electrode signals are affected by respiration.

It is known in the art that a respiratory signal can be derived from the modulation caused by respiration in the electrode data of cardiac electrode activity. For example, in terms of the equivalent dipole model of cardiac electrical activity, respiration induces an apparent modulation in the direction of the mean cardiac electrical axis. Therefore, frequency of respiration can be determined from an exemplary system, according to the present disclosure.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessarily represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A system comprising;
an apparatus comprising a first layer and a second layer, the first layer configured to collect pressure data, and the second layer comprising a plurality of electrodes;
a processing unit communicatively coupled to the apparatus, the processing unit configured to:
receive pressure data from the first layer;
determine an orientation of a user based on the received pressure data;
select a subset of electrodes from the plurality of electrodes based on the determined orientation; and
measure electrical activity at the subset of electrodes.

2. The system of claim 1, wherein the plurality of electrodes comprise dry electrodes integrated into the second layer with woven conductive thread.

3. The system of claim 1, wherein the received pressure data comprises two-dimensional coordinates of pressure applied by the user to the first layer.

4. The system of claim 3, wherein determining an orientation of the user further comprises:
placing the received pressure data in a coordinate grid, the coordinate grid corresponding to the first layer;
identifying a body position of the user based on locations of the placed pressure data in the coordinate grid.

5. The system of claim 4, wherein identifying a body position of the user further comprises:
classifying the placed pressure data in the coordinate grid to generate a set of validated body positions for the user, wherein classifying the placed pressure data comprises using a machine learning classifier to classify the placed pressure data as valid or invalid for each body position in a plurality of body positions; and
outputting a set of valid body positions.

6. The system of claim 5, wherein selecting a subset of electrodes further comprises selecting corresponding electrodes based on the identified body position and the locations of the placed pressure data.

7. The system of claim 1, wherein measuring electrical activity further comprises generating at least one of: a bipolar limb lead, a unipolar limb lead, and a unipolar chest lead.

8. The system of claim 1, wherein the apparatus is a bed sheet.

9. The system of claim 1, wherein the processing unit is further configured to output an electrocardiogram based on the measured electrical activity.

10. The system of claim 1, wherein the first layer comprises at least one of: a microelectromechanical system sensor, a board mounted sensor, and a heavy-duty pressure transducer.

11. The system of claim 1, wherein the processing unit, based on the measured electrical activity, is further configured to output at least one of:
measured electrodermal activity of the user;
an electroencephalogram; and
an electromyogram.

12. A system comprising;
a sheet configured to collect pressure data and comprising a plurality of electrodes;
a processing unit communicatively coupled to the apparatus, the processing unit configured to:
receive pressure data from the sheet;
determine an orientation of a user based on the received pressure data;
select a subset of electrodes from the plurality of electrodes based on the determined orientation; and
measure electrical activity at the subset of electrodes.

13. A method comprising:
receiving pressure data from an apparatus comprising a plurality of electrodes;
determining an orientation of a user based on the received pressure data;
selecting a subset of electrodes from the plurality of electrodes based on the determined orientation; and
measuring electrical activity at the subset of electrodes.

14. The method of claim 13, wherein the apparatus comprises a first layer and a second layer, the first layer configured to receive pressure data and the second layer comprising a plurality of dry electrodes integrated into the second layer with woven conductive thread.

15. The method of claim 13, wherein the received pressure data comprises two-dimensional coordinates of pressure applied by the user to the first layer.

16. The method of claim 13, wherein determining an orientation of the user further comprises:
   placing the received pressure data in a coordinate grid, the coordinate grid corresponding to the first layer;
   identifying a body position of the user based on locations of the placed pressure data in the coordinate grid.

17. The method of claim 16, wherein identifying body parts of the user further comprises:
   classifying the placed pressure data in the coordinate grid to generate a set of validated body positions for the user, wherein classifying the placed pressure data comprises using a machine learning classifier to classify the placed pressure data as valid or invalid for each body position in a plurality of body positions; and
   outputting a set of valid body positions.

18. The method of claim 17, wherein selecting a subset of electrodes further comprises assigning corresponding electrodes based on the identified body position and the locations of the placed pressure data.

19. The method of claim 13, wherein the method further comprises outputting at least one of:
   an electrocardiogram;
   measured electrodermal activity of the user;
   an electroencephalogram; and
   an electromyogram.

20. The method of claim 13, wherein the first layer comprises at least one of: a microelectromechanical system sensor, a board mounted sensor, and a heavy-duty pressure transducer.

* * * * *